United States Patent
Gwenin et al.

(10) Patent No.: US 9,089,613 B2
(45) Date of Patent: Jul. 28, 2015

(54) DRUG ACTIVATION SYSTEM

(75) Inventors: Christopher Gwenin, Nant Peris (GB); Maher Kalaji, South Lake Tahoe, CA (US); Vanessa Roberts, Nant Peris (GB)

(73) Assignee: BANGOR UNIVERSITY, Bangor, Gwynedd (GB)

( * ) Notice: Subject to any disclaimer, the term of this patent is extended or adjusted under 35 U.S.C. 154(b) by 572 days.

(21) Appl. No.: 13/393,995

(22) PCT Filed: Sep. 2, 2010

(86) PCT No.: PCT/EP2010/062871
§ 371 (c)(1),
(2), (4) Date: May 22, 2012

(87) PCT Pub. No.: WO2011/026898
PCT Pub. Date: Mar. 10, 2011

(65) Prior Publication Data
US 2012/0232328 A1 Sep. 13, 2012

(30) Foreign Application Priority Data
Sep. 2, 2009 (GB) .................................. 0915249.7

(51) Int. Cl.
*C12M 1/34* (2006.01)
*A61K 47/48* (2006.01)
*B82Y 5/00* (2011.01)

(52) U.S. Cl.
CPC ..... *A61K 47/48361* (2013.01); *A61K 47/48861* (2013.01); *B82Y 5/00* (2013.01)

(58) Field of Classification Search
CPC .............................................. A61K 47/48361
USPC ....................................................... 435/287.1
See application file for complete search history.

(56) References Cited

FOREIGN PATENT DOCUMENTS

WO  WO 00/47725     8/2000
WO  WO 03/018788    3/2003
WO  WO 2006/103452  10/2006

OTHER PUBLICATIONS

Rooseboom et al. "Enzyme-catalyzed activation of anticancer prodrugs", Pharmacological Reviews, 2004, 56(1):53-102.*
Alexiou et al., "Targeting cancer cells: magnetic nanoparticles as drug carriers," Eur. Biophys. Journal, 35, 446-450, 2006.
Anlezark et al., "The bioactivation of 5-(Aziridin-1-yl)-2,4-Dinitrobenzamide (CB1954)-I," Biochemical Pharmacology 44, 2289-2295, 1992.
Asche et al., "Nitrobenzylacarbamate prodrugs of cytotoxic acridines for potential use with nitroreductase gene-directed enzyme prodrug therapy," Bioorganic and Medicinal Chemistry Letter 16, 1990-1994, 2006.
Mayer et al. "A phase I study of single administration of antibody-directed enzyme prodrug therapy with the recombinant anti-carcinoembryonic antigen antibody-enzyme fusion protein MFECP1 and a bis-Iodo phenol mustard prodrug," Clinical Cancer Research 12, 6509-6516, 2006.
Bagshawe in Prodrugs, eds. Stella et al., vol. V, Part II, Part 5, pp. 525-540, Springer, New York, New York; 2007.
Behr, "Gene transfer with synthetic cationic amphiphiles: prospects for gene therapy," Bioconjugate Chem. 5, 382-389, 1994.
Chah et al., "Gold nanoparticles as a colorimetric sensor for protein conformational changes," Chemistry and Biology 12, 323-328, 2005.
Gwenin et al., "The orientationally controlled assembly of genetically modified enzymes in an amperometric biosensor," Biosensors and Bioelectronics, 22, 2869-2875, 2007.
Kohler et al., "Methotrexated-modified superparamagnetic nanoparticles and their intracellular uptake into human cancer cells," Langmuir 21, 8858-8864, 2005.
Kohler et al., "Methotrexated-immobilized poly(ethylene glycol) magnetic nanoparticles for MR imaging and drug delivery," Small 2, 785-792, 2006.
Kratz et al., "Prodrug strategies in anticancer chemotherapy," Chem. Med. Chem. 3, 20-53, 2008.
Lovering et al., "The structure of *Escherichia coli* nitroreductase complexed with nicotinic acid: three crystal forms at 1.7 Å, 1.8 Å and 2.4 Å resolution," Journal of Molecular Biology 309, 203-213, 2001.
Massart, "Preparation of aqueous magnetic liquids in alkaline and acidic media," IEEE Trans. Magn. 1981, 17(2), 1247-1248.
Race et al., "Kinetic and structural characterization of *Escherichia coli* nitroreductase mutants showing improved efficacy for the prodrug substrate CB1954," Journal of Molecular Biology, 368, 481-492, (2007).
Reimer et al., "Hepatic MRI with SPIO: detection and characterization of focal liver lesions," Eur. J. Radiol. 8, 1198-1204, 1998.
Ros et al., "Hepatic MR imaging with ferumoxides: a multicenter clinical trial of the safety and efficacy in the detection of focal hepatic lesions," Radiology 196, 481-488, 1995.
Schepelmann et al., "Viral vectors for gene-directed enzyme prodrug therapy," Current Gene Therapy 6, 647-670, 2006.
Sharma et al., "DNA-templated self-assembly of two-dimensional and periodical gold nanoparticle arrays," Angew. Chem. Int. Ed. 45, 730-735, 2006.
Searle et al., "Nitroreductase: a prodrug-activating enzyme for cancer gene therapy," Clinical and Experimental Pharmacology and Physiology, 31, 811-816, 2004.

(Continued)

Primary Examiner — Bin Shen
(74) Attorney, Agent, or Firm — RatnerPrestia

(57) ABSTRACT

The present invention discloses a drug activator carrier comprising: a) particles having a metallic or metallic oxide core prepared from a paramagnetic material, said metallic core being coated with a coating material selected from polymer, metal or metal oxide; b) a biological material, having reductase activity, bound onto the metal coating the particles of step a), and wherein said biological material is capable of activating non-toxic pro-drugs into active and toxic drugs suitable for treating a disease; said drug activator carrier allowing targeted delivery of the toxic drug.

16 Claims, 8 Drawing Sheets

(56) References Cited

OTHER PUBLICATIONS

Wadhwa et al., "Pepide-mediated gene delivery: influence of peptide structure on gene expression," Bioconjugate Chem. 8, 81-88, 1997.

Weissleder et al., "Superparamagnetic Iron Oxide: pharmacokinetics and toxicity," American Journal of Roentenology 152, 167-173, 1989,.

Yokomaya et al., "The conjugation of amyloid beta protein on the gold colloidal nanoparticles," Nanotechnology 18, 1-7, 2007.

Zenno et al., "Gene cloning, purification, and characterization of NfsB, a minor oxygen insensitive nitroreductase from *Escherichia coli*, similar in biochemical properties to FRase I, the major flavin reductase in vibrio fischeri," Journal of Biochemistry 120, 736-744, 1996.

Zhuo et al., "Bienxyme functionalized three-layer composite magnetic nanoparticles for electrochemical immunosensors," Biomaterials, vol. 30, No. 12, 2009, pp. 2284-2290.

Gwenin et al., "Viscoelastic change following adsorption and subsequent molecular reorganization of nitroreductase enzyme on a gold surface: A QCM study," Sensors and Actuators B, vol. 126, No. 2, pp. 499-507, 2007.

Lyon et al., "Synthesis of fe oxide core/au shell nanoparticles by iterative hydroxylamine seeding," Nano Letters, vol. 4, No. 4, 2004, pp. 719-723.

Hanfland et al., "Optical properties of metallic silicon," Physical Review, B. Condensed Matter, vol. 38, No. 18, 1988, pp. 12864-12867.

\* cited by examiner

PRIOR ART

DRUG ACTIVATION SYSTEM

CROSS-REFERENCE TO RELATED APPLICATIONS

This application is the U.S. National Phase application of PCT International Application No. PCT/EP2010/062871, filed Sep. 2, 2010, and claims priority of British Patent Application No. 0915249.7, filed Sep. 2, 2009, the disclosures of both of which are incorporated herein by reference in their entireties for all purposes.

BACKGROUND OF THE INVENTION

1. Field of the Invention

The present invention relates to a drug activation system efficient for targeted drug delivery into the human body.

2. Description of the Related Art

Many anti-cancer drugs kill dividing cells to prevent uncontrolled growth of malignant cells. Systemic application of such drugs can also damage healthy cells resulting in serious side effects and the development of therapy-induced tumours. Directed enzyme prodrug therapy (DEPT) is based on the targeted delivery of enzymes directly to the malignant growth, where the enzymes convert a harmless prodrug into a cytotoxic drug.

To try and further increase tumour selectivity, research has recently focused on using tumour specific antigens to target the drug/prodrug directly to the solid tumour as disclosed for example in Kratz et al. (Kratz, F., Muller, I. A., Ryppa, C. & Warnecke, A., *Chem Med Chem* 3, 20-53, 2008).

Another selective approach targets the prodrug-activating enzyme or its encoding gene to the tumour before administering the prodrug, using carriers such as antibodies, viruses, cationic lipids, peptides, or naked DNA, as disclosed for example in Bagshawe (Bagshawe, K. D. in Prodrugs, Vol. V., eds. V. J. Stella et al., Springer New York, N.Y.; 2007) or in Schepelmann and Springer. (Schepelmann, S. & Springer, C. J. in *Current Gene Therapy* 6, 647-670, 2006), or in Behr (Behr, J.-P., *Bioconjugate Chem* 5, 382-389, 1994), or in Wadhwa et al. (Wadhwa, M. S., Collard, W. T., Adami, R. C., McKenzie, D. L. & Rice, K. G., in *Bioconjugate Chem* 8, 81-88, 1997).

The limitations of the above mentioned methods are the scarcity of tumour specific antigens, the immunogenicity of the drug-carrier combination, and the inefficient expression of enzymes from the targeted DNA.

A different approach for targeted chemotherapy is the use of magnetic nanoparticles (MNPs), which can be directed to the tumour using an external magnetic field. Additionally, treatment localisation and progress can be monitored using real-time Magnetic resonance (MR) imaging. The most common MNPs investigated for cancer therapy has been iron oxide nanoparticles, due to their low toxicity, and approval by the Food and Drug Administration. Such methods have been described for example in Alexiou et al. (Alexiou, C. et al. in *Eur Biophys J Biophy* 35, 446-450, 2006), or in Kohler et al. (Kohler, N., Sun, C., Wang, J. & Zhang, M. in *Langmuir* 21, 8858-8864, 2005), or in Kohler et al. (Kohler, N. et al. in *Small* 2, 785-792, 2006), or in Weissleder et al. (Weissleder, R. et al. In *American Journal of Roentenology* 152, 167-173, 1989) or in Ros et al. (Ros, P. R. et al. in *Radiology* 196, 481-488, 1995), or in Reimer and Tombach (Reimer, P. & Tombach, B. in *Eur J Radiol* 8, 1198-1204, 1998).

Research into the use of bacterial nitroreductases (NTRs) in DEPT has focused on the use of enzymes such as *Escherichia Coli* (*E. coli*) to activate dinitrobenzamide prodrugs at solid tumours, as described for example in Searle et al. (Searle P. F., M. J. Chen, L. Hu, P. R. Race, A. L. Lovering, J. I. Grove, C. Guise, M. Jaberipour, N. D. James, V. Mautner, L. S. Young, D. J. Kerr, A. Mountain, S. A. White, and E. I. Hyde, in *Clinical and Experimental Pharmacology and Physiology*, 31, 811-816, (2004). However, viral vectors still lack specificity and the slow turnover rate of the studied prodrugs limits the therapeutic efficacy of this NTR/prodrug combination in DEPT as explained for example in Astrimayer et al. (Astridmayer, R. Francis, S. K. Sharma, Berendtolner, C. Springer, J. Martin, G. Boxer, J. Bell, A. Green, J. A. Hartley, C. Cruickshank, Juliewren, K. Chester, and R. H. J. Begent. in *Clinical Cancer Research*. 12: 6509-6516, (2006).

Attempts to improve the kinetic abilities of these enzymes by site-directed mutagenesis were reported by Race et al. (Race P. R., A. L. Lovering, S. A. White, J. I. Grove, P. F. Searle, C. W. Wrighton, and E. I. Hyde, in *Journal of Molecular Biology*. 368, 481-492, (2007).

The synthesis of novel prodrugs has also been reported in Anlezark et al. (Anlezark G. M., R. G. Melton, R. F. Sherwood, B. Coles, F. Friedlos, and R. J. Knox. In *Biochemical Pharmacology*. 44: 2289-2295 (1992) or in Asche et al. (Asche C., P. Dumy, D. L. Carrez, A. Croisyb, and M. Demeunyncka. in *Bioorganic and Medicinal Chemistry Letters*. 16: 1990-1994, (2006). This has resulted in substantial improvements, but the enhanced kinetic parameters may still limit clinical efficacy. These studies suggest that other bacterial species may have increased catalytic efficiencies better suited for DEPT.

There is thus a need to improve the delivery of drugs directly to the diseased cells.

SUMMARY OF THE INVENTION

It is an objective of the present invention to prepare a prodrug activator allowing the targeted delivery of drugs.

It is another objective of the present invention to develop new nitroreductases from different bacterial species.

It is also an objective of the present invention to develop cofactors other than the usually used nicotinamide adenine dinucleotides (NAD) in order to allow the use of a larger selection of prodrugs.

In accordance with the present invention, the foregoing objectives are realised as defined in the independent claims. Preferred embodiments are defined in the dependent claims.

DETAILED DESCRIPTION OF THE INVENTION

Accordingly, the present invention discloses a drug activator carrier comprising:
a) nanoparticles having a metallic or metallic oxide core prepared from a paramagnetic material, said metallic core being coated with another material, said coating material being selected for example from polymer, metal or metal oxide;
b) a biological material, having reductase activity, bound onto the coating of the particles of step a), and wherein said biological material is capable of activating nontoxic prodrugs into active and toxic drugs suitable for treating a disease; said drug activator carrier allowing targeted delivery of the toxic drug.

The drug activator carrier is suspended in a solution for easy injection. It is then directed by means of a magnetic field gradient towards the desired location where it transforms the non toxic prodrug into an active drug. The nontoxic prodrug is introduced in the blood stream and to the infected area prior to the introduction of the drug activator carrier.

In a preferred embodiment according to the present invention, the paramagnetic nanoparticles are prepared from iron, nickel or cobalt, more preferably from iron or their oxides or combinations thereof. The paramagnetic particle size is of at most 100 nm, preferably of at most 50 nm, and more preferably of 30 nm or less.

The coating material is preferably a noble metal selected from the group consisting of gold, silver, platinum, palladium, iridium, rhenium, ruthenium, or alloys or polymers or combinations thereof. More preferably it is gold.

The thickness of the coating layer is homogeneous and is of the order of a few nm.

The size of the coated particles is of at most 100 nm, preferably of at most 50 nm in order to access and penetrate the diseased cells to be treated.

The biological material is immobilised on the coating layer. It is preferably a protein.

The protein can be selected from an enzyme, antibody, receptor, antibody fragment or binding protein. More preferably it is an enzyme and even more preferably a nitroreductase. The enzyme is preferably modified by adding reactive groups. These reactive groups serve the purpose of creating strong bonds between the enzyme and the coating.

Figure 1:
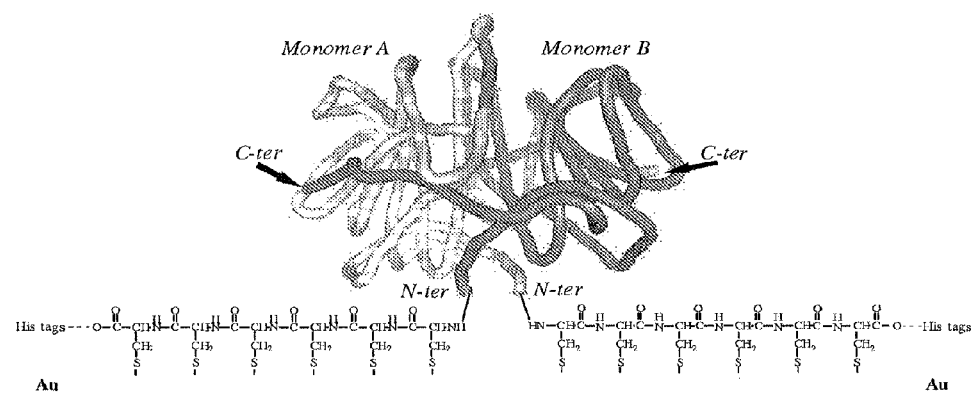
FIG. 1 illustrates the $cys_{12}$ tags immobilising the dimeric nitroreductase via the N-terminus on a gold surface, drawn with PyMOL software.

In the pair sulphur/gold, the enzyme is modified by adding a plurality of sulphur-containing reactive groups such as for example 12 cysteine tags. Preferably, they are sulphydryl (—SH) groups. In a preferred embodiment according to the present invention, the nitroreductase is immobilised onto the gold surface through a plurality of cysteine amino acids, for example a sequence of six cysteine amino acids ($Cys_6$), which have been genetically incorporated into the native enzyme. The resulting gold thiolate bonds (Au—S) result in strong coupling between enzyme and gold and highly stable monolayers. This self-assembled structure has the main advantage of being easily reproducible and of offering a high degree of control over the molecular architecture. It is important to immobilise the enzyme with an orientation that does not inhibit the active site, either through physical restriction or conformational changes. For that purpose and for example, the $Cys_6$ sequence is introduced at the N-terminus of each monomer adjacent to a standard $His_6$ tag. FIG. 1 is a pictorial representation of the dimeric nitroreductase immobilised via the N-terminus $Cys_6$ tags onto a gold surface, (drawn with PyMOL). The preparation of the modified enzyme used in the present invention has been described for example in Gwenin et al. (Gwenin C. D., Kalaji M., Williams P. A., Jones R. M. in Biosens. Bioelectron. (2007), doi:10.1016/j.bios.2006.12.012).

The ratio of enzyme to gold ranges between 100:1 and 500:1, preferably between 200:1 and 400:1 and more preferably between 250:1 and 300:1.

The amount of immobilised NTR enzymes is quantified by stripping voltammetry on the modified gold nanoparticles. The charge associated with cathodic stripping of thiols provides the number of reduced thiol bonds.

The technology of attaching nitroreductases to gold-coated magnetic nanoparticles (MNP) allows direct targeting of the enzyme to solid tumours by means of a magnetic field gradient, after which the coated particles and the pro-drug are taken up by cells resulting in their death. The use of MNPs with a gold surface provides an interesting class of biomaterials that enables the overcoming of obstacles such as surface fouling seen in regular magnetic particles and polymer composites.

Nitroreductases are homodimeric flavoproteins in which the flavin mononucleotide cofactor is oxidised by nicotinamide adenine dinucleotide (NAD(P)H) and which, in turn, reduces a variety of nitroaromatic and quinone substrates.

Suitably, the nitroreductase can be selected from Bacterial NTRs for example from *Escherichia coli*, *Bacillus licheniformis*, *Pseudomonas putida*, or *Salmonella* sp. As *Escherichia coli* is easily available, and has been studied and described in many publications, it is used as reference.

Suitably, the prodrugs can be selected from (5-aziridin-1-yl)-2,4-dinitrobenzamide, known as CB1954, dinitrobenzamide mustards, and 4-dinitrobenzyl carbamates.

Figure 2:
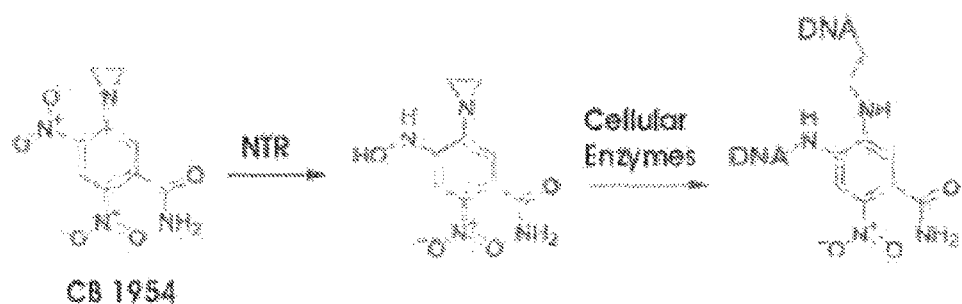
FIG. 2 illustrates the mechanism whereby CB1954 can be converted into a powerful DNA crosslinking agent upon reduction of one of the two nitro groups as disclosed for example in Anlezark et al. (Anlezark G. M., R. G. Melton, R. F. Sherwood, B. Coles, F. Friedlos, and R. J. Knox, in *Biochemical Pharmacology*. 44: 2289-2295, 1992)

The best known example of a prodrug activated by nitroreductase is CB1954, which is converted into a powerful interstrand DNA crosslinking agent after reduction of either its 2- or 4-nitro group as represented in FIG. 2. The toxicity of CB1954 is due to the low repair efficiency of DNA crosslinks and to the sensitivity of both, replicating and non-replicating cells. In addition, bystander effects emanating from the use of the CB1954 prodrug result in the killing of cancer cells which are generally not accessible by direct drug delivery. CB1954 is used as reference prodrug.

The ability of the different nitroreductases to metabolise the selected prodrugs is assessed as the conversion of NADH to $NAD^+$ by UV-vis spectra. The kinetic parameters of the purified enzymes are measured by UV-vis spectra before and after their attachment to gold particles based on their ability to use NADH or an alternative cofactor such as for example nicotinic acid riboside for the reduction of the prodrugs.

One of the main applications of this invention is the adenovirus based deliveries of the nitroreductase to activate prodrugs at solid tumours. The non toxic prodrug is injected into the blood stream first; the magnetic carrier is then directed to the solid tumour where it activates the non toxic prodrug into an active toxic drug. The half life of the activated prodrug is of the order of a few seconds.

The present invention also discloses a method for preparing the drug activating carrier of the present invention that comprises the steps of:
a) providing nanoparticles of a paramagnetic material;
b) coating said particles with a metal or polymer or metal oxide;
c) immobilising an enzyme capable of transforming a non toxic prodrug into an active and toxic drug for treating a disease by chemical bonding between the enzyme and the coating material.

The present invention further discloses the use of the drug activating carriers of the present invention to deliver an active drug to the desired position by applying a magnetic field gradient.

EXAMPLES

Preparation of Enzyme-Coated Gold Colloid

The NfnB-cys12 protein was expressed and purified as described in Gwenin et al. (Gwenin C. D., M. Kalaji, P. A. Williams, and R. M. Jones. In *Biosensors and Bioelectronics*. 22: 2869-2875, 2007). The wildtype NfnB gene (gene ID: 945778) from *Escherichia coli* K12 (Genbank accession number NC_00913) was amplified from genomic DNA using designed primers during a PCR protocol. To generate the cys-NfnB gene, a Cysteine tag was introduced during PCR by using a primer coding for 6 Cysteine residues downstream from the NfnB start codon. Both the wildtype (NfnB) and modified (cys-NfnB) genes were then cloned into the pET28a(+) expression vector (Novagen, Merck, UK) which added an N-terminal Histidine-tag (his-tag) for ease of purification of the proteins. The proteins were next expressed by an *E. coli* Rosetta™ strain (Novagen, UK) transformed with the recombinant NfnB and cys-NfnB plasmids. The his-tagged NfnB and cys-NfnB proteins were purified from the cell debris by centrifugation and metal ion affinity chromatography before finally removing small molecule contaminants with ultra pure water during size exclusion chromatography. The purity and molecular weight of the protein fractions were always assessed by 12% SDS-PAGE before use in further experiments. Protein concentration was determined from a BSA standard curve using the ProPure Biuret protein assay (Amresco, NBS Biologicals, UK) according to the manufacturer's instructions. The protein concentration was of 6 mg/ml.

Figure 3:
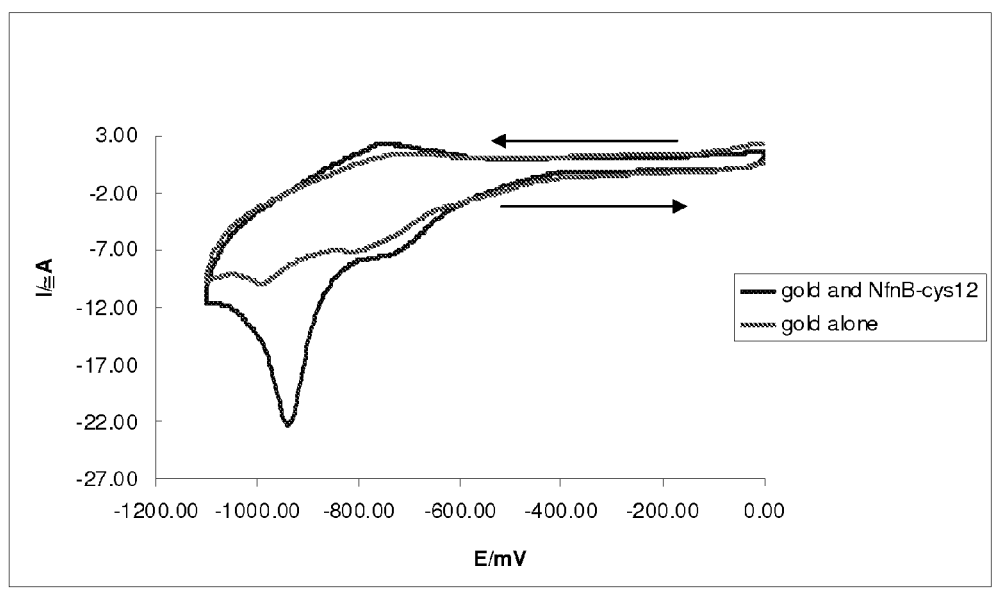
FIG. 3 represents the voltammogram at a sweep rate of 50 mV/s in a 0.1 M solution of NaOH; the working electrode was the modified (NfnB-cys12) Au(111) coated glass slide after incubation. Scans show the gold, alone and after incubation with NfnB-cys12.

A gold coated glass slide was then incubated in the enzyme solution overnight and cyclic voltammetry was performed. A saturated calomel electrode served as the reference electrode while a platinum electrode served as the counter electrode. The voltammograms, respectively of gold alone and of gold and enzyme, obtained using a sweep rate of 50 mV/s, are represented in FIG. 3.

Coating 20 Nm Gold Colloid Particles with NfnB-Cys12.

After showing that the NfnB-cys12 enzyme purified with the cys-tags was capable of binding to gold, the 20 nm gold colloid ($1.1624 \times 10^{-3}$ nmol/ml, suspended in water, BBInternational) was incubated, at room temperature (18° C.) for 1 hour or at 4° C. for 17 hours, with varying ratios of enzyme concentrations as described for example in Chah et al. (Chah S., M. R. Hammond, and R. N. Zare., in *Chemistry and Biology*. 12: 323-328, 2005) or in Yokoyama and Welchons (Yokoyama K., and D. R. Welchons., in *Nanotechnology*. 18: 105101, 2007). The total volume of the mixtures was always kept constant so that the gold concentration remained constant. The interaction of enzyme with the surface of the colloidal gold particles was investigated by comparing the absorption spectra (750 nm-200 nm) of the colloidal gold before and after incubation with either NfnB or cys-NfnB. Spectra were recorded on a Jasco V-550, UV/Vis spectrophotometer and analysed with the spectra manager software.

The NfnB-cys12 protein solution (125 nmol/ml in PB buffer, pH=7.2) was purified and desalted as previously described in Gwenin et al. (Gwenin C. D., M. Kalaji, P. A. Williams, and R. M. Jones, in *Biosensors and Bioelectronics*. 22: 2869-2875, 2007). Table 1 displays the molar ratio enzyme/gold and the concentrations of gold colloid and enzyme that were studied.

TABLE 1

| molar ratio enzyme/gold | Amount of enzyme solution added (nmol) | Amount of gold colloid added (ml) | Final concentration of gold colloid (nmol/ml) | Final concentration of enzyme (nmol/ml) |
| --- | --- | --- | --- | --- |
| 5:1 | 0.011 | 2 | 0.0011 | 0.0052 |
| 100:1 | 0.232 | 2 | 0.0011 | 0.106 |
| 500:1 | 1.1624 | 2 | 0.0011 | 0.555 |
| 1000:1 | 2.3248 | 2 | 0.00106 | 1.064 |
| 10 000:1 | 23.248 | 2 | 0.00106 | 10.64 |

The 20 nm gold colloid was incubated for a period of time of one hour, with or without NfnB-cys12 and the UV-vis spectra were recorded in the spectral range of 750 to 250 nm. Knowing that the 20 nm gold colloid absorbs at a wavelength of 524 nm in phosphate buffer (PB) having a pH of 7.2, any changes in the Localised Surface Plasmon Resonance (LSPR) peak of the gold were noted and reported after incubation with the enzyme. The results are reported in FIG. 4 where it is observed that for NfnB-cys12: gold ratio of 100:1, the 524 nm peak of gold alone is shifted to 529 nm in the presence of enzyme.

Figure 4:
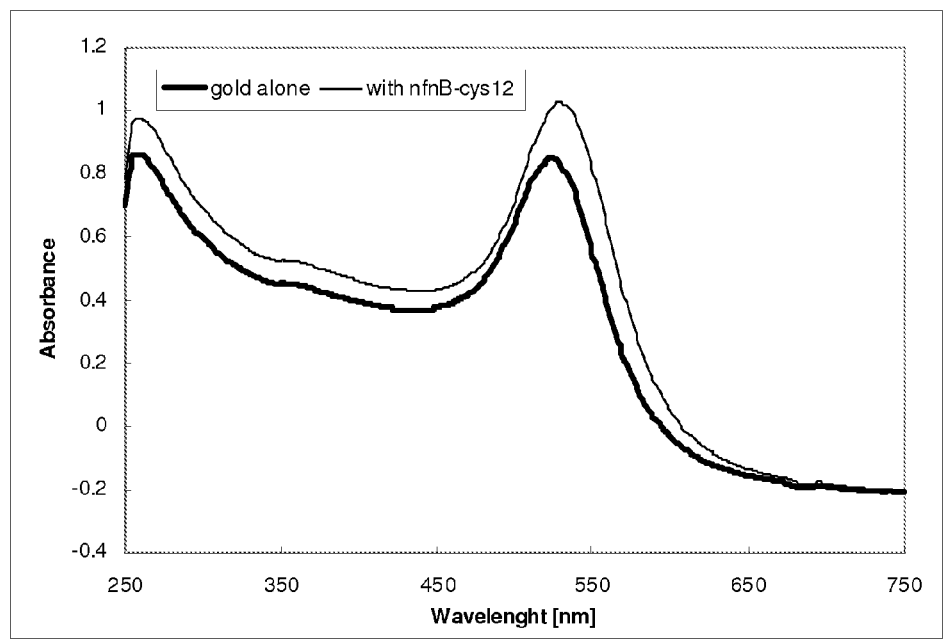
FIG. 4 represents the change in LSPR peak for colloidal gold (20 nm particles) alone and in presence of NfnB-cys12 with a NfnB-cys12: gold ratio of 100:1 after 1 hour of incubation. Peak changes from 524 nm in absence of enzyme to 529 nm in presence of enzyme. The solid line represents gold alone and the dashed line represents gold and enzyme.
Figure 5:
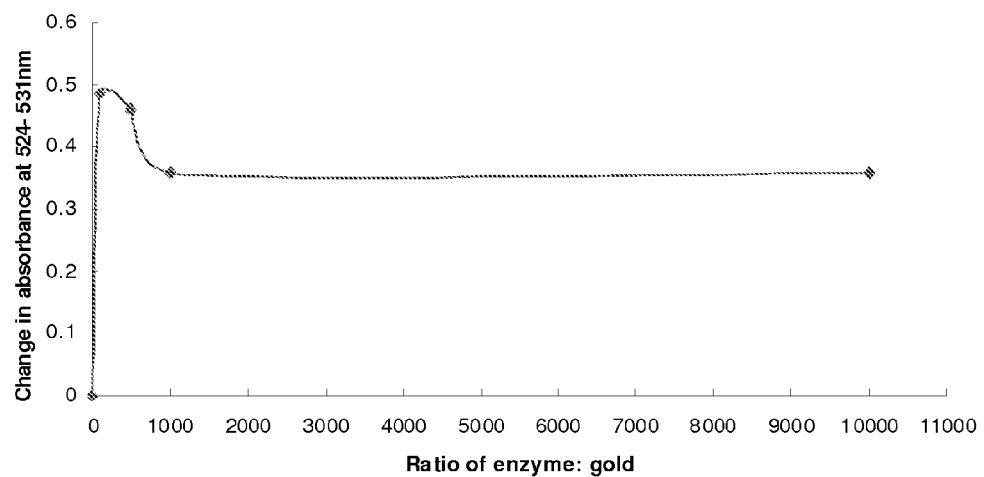
FIG. 5 represents the change in colloidal gold LSPR peak intensity as a function of NfnB-cys12: gold ratio in the 524-531 nm region for 20 nm gold particles.

As can been seen from FIG. 4, the wavelength at which the colloidal gold absorbs light was changed in the presence of the enzyme. This change in LSPR was observed at all ratios of enzyme: gold, which indicates that protein has bound to the gold surface. As can be seen from FIG. 5, the greatest intensity was achieved for an enzyme to gold molar ratio of 100:1. The peak intensity dropped slightly with increasing enzyme to gold ratios and became stable for enzyme to gold ratios of 500:1 or more. These results suggest that the optimal enzyme to gold ratio is of 100:1 when used to coat 20 nm colloidal gold nanoparticles.

In order to further determine whether enzyme has immobilised onto the gold surface, agarose gel electrophoresis was performed for the 20 nm gold colloid both in the absence and in the presence of NfnB-cys12, using the method of Sharma et al. (Sharma J., R. Chhabra, Yan Liu, Y. Ke, and H. Yan., in *Angew. Chem. Int. Ed.* 45: 730-735, 2006) modified by changing the percentage composition of the gel and the percentage composition of the glycerol used for loading the gel. A 2.5% agarose gel was prepared and loaded with samples (30 μl). Samples were prepared by adding 25 μl of colloidal gold solution to 5 μl of loading buffer followed by mixing. The loading buffer consisted of glycerol (5 ml), 0.5M Tris HCl (2.5 ml) of pH 8.8, and 10% sodium dodecyl sulphate (SDS) (2.5 ml). The gel was run at 220 V for 60 min. The results are displayed in FIG. 6 representing a 2.5% agarose gel indicating the difference in migration of 20 nm gold colloid nanoparticles before and after incubation with different concentrations of NfnB-cys12 enzyme.

Figure 6:
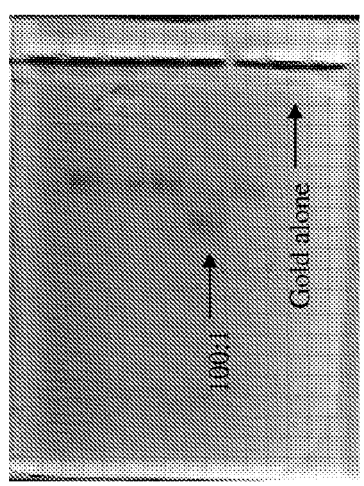
FIG. 6 represents the 2.5% agarose gel electrophoresis indicating the difference in migration of 20 nm gold colloid nanoparticles before and after incubation with different concentrations of NfnB-cys12 enzyme for ratios of enzyme: gold varied between 5:1 and 10000:1. Lane 1 is a blank, lane 2 represents an enzyme to gold ratio of 10000:1, lane 3 of 1000:1, lane 4 of 500:1, lane 5 of 100:1, lane 6 of 5:1, lane 7 of gold alone, and lane 8 a blank.

As can be seen from FIG. 6, the colloidal gold alone migrates very little in the presence of an applied potential, but all the enzyme-coated colloidal gold samples, migrate into the agarose gel when subjected to an applied field of 220 V. The 100:1 enzyme: gold ratio solution migrates the furthest into the agarose gel, suggesting that at this ratio of enzyme to gold, the gold particles are coated optimally. Without wishing to be bound by a theory, it is believed that the difference in migration of the enzyme/gold conjugate is an indication of surface coverage and overall charge of the conjugate.

The 5:1 and 100:1 enzyme: colloidal gold solutions have been further studied by transmission electron microscopy in order to further assess the binding of NfnB-cys12 to the gold nanoparticles.

Conjugate Stability

NfnB and cys-NfnB enzyme: gold conjugates were prepared by incubating respectively 100, 200, 300, 400 and 500 molar equivalents of enzyme, in water, with 1.5 ml of 1.4× $10^{-3}$ μM 20 nm Naked Gold® (BioAssay Works, USA), and made up to a final volume of 2 ml using ultra pure water having a pH of about 7. The enzyme: colloidal gold solutions were allowed to incubate for 17 hours at a temperature of 4° C. The effect of the pH on the stability of the enzyme: gold conjugates and colloidal gold alone was assessed by adding 200 μl of conjugate samples or gold colloid to 600 μl cuvettes containing buffered phosphate solutions of pH ranging between 2 and 11. They were incubated for 15 min before measuring their absorbance spectra (750 nm-200 nm) using water as reference.

The absence of a wavelength shift serves as a clear indication that the colloidal system has been stabilised by the enzyme coating.

Figure 7:
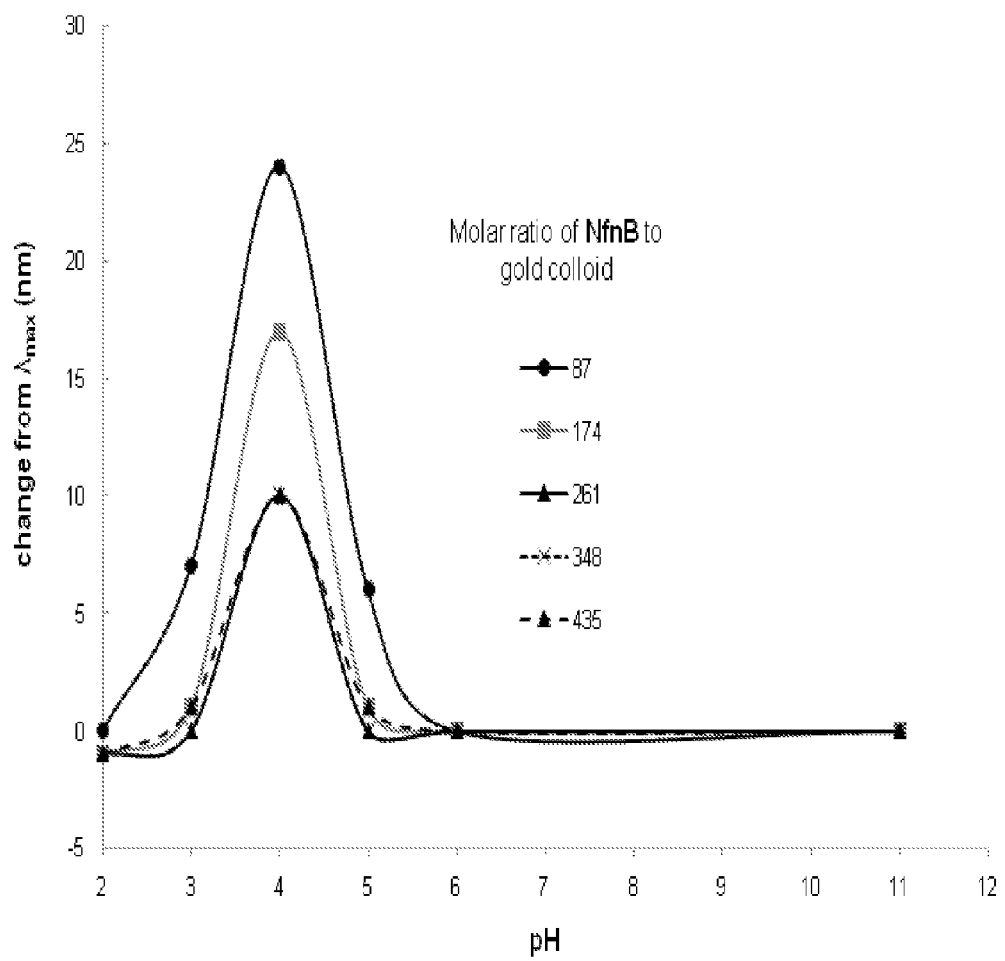
FIG. 7 represents the deviation of $\lambda_{max}$, expressed in nm as a function of pH for different molar ratios of NfnB to gold.

As seen from FIG. 7, all the conjugates were stable at or above a pH of 6 and at pH=2 and 3. The stability profiles in changing pH conditions were the same for both the NfnB or cys-NfnB conjugates. It was however observed that, conjugates formed at a temperature of 4° C. overnight had a higher stability than that of conjugates formed at a temperature of 25° C. for 1 hour. Stability of the conjugates also depended on the degree of surface coverage of the gold nanoparticle. Colloidal gold was only stable in the range of pH from 4 to 1 due to the negative charge of the surface associated citrate, stabilising the gold hydrosol.

To assess the ability of the conjugates to resist a change in the ionic environment, a range of enzyme: gold conjugates were prepared by incubating purified NfnB or cys-NfnB solutions, in water, with 500 μl of 2×$10^{-3}$ μM 20 nm Naked Gold® (in water) in molar ratios of 100, 200, 300, 400, and 500:1 enzyme:gold colloid. All samples were made up to the same final volume using ultra pure water having a pH of about 7 so as to keep the gold colloid concentration the same. Samples were then incubated overnight at a temperature of 4° C. The next day, spectra (750 nm-200 nm) of 800 μl of the conjugates and gold colloid were analysed by UV/Vis spectrometry as the concentration of NaCl was increased every 15 min from 0 M-5M. All spectra were measured using ultra pure water as reference.

Figure 8:
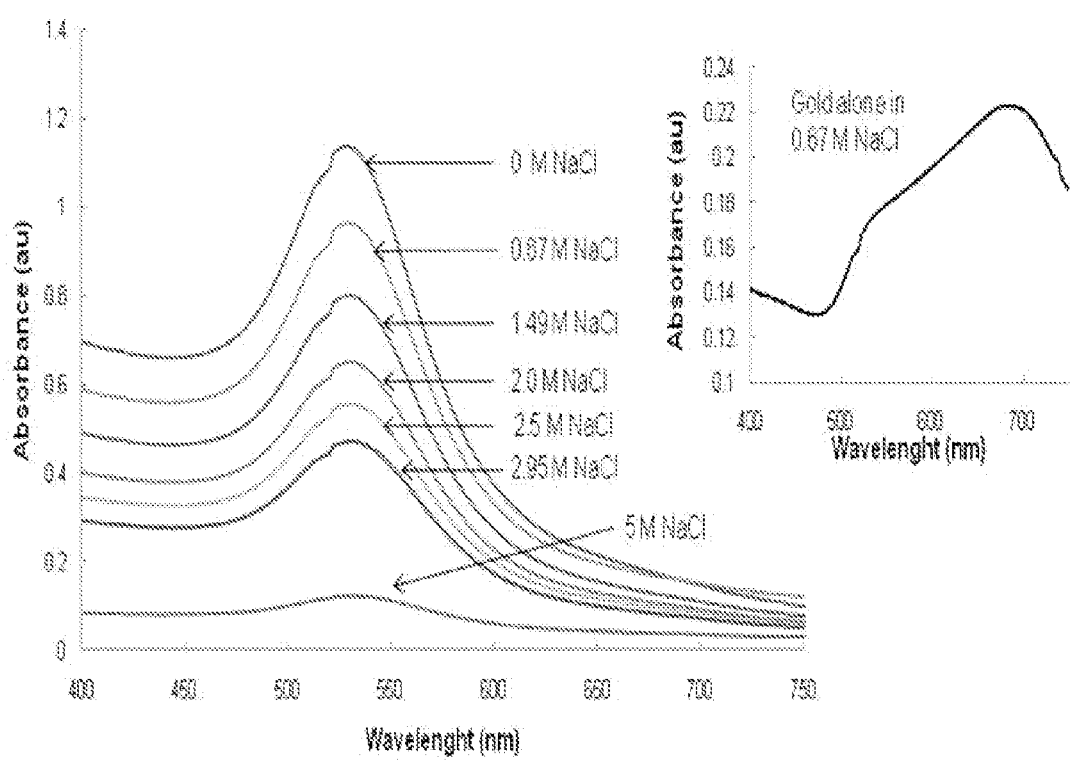
FIG. 8 represents the absorbance expressed in absorbance units (au) as a function of wavelength expressed in nm for various additions of NaCl.

In the absence of conjugated enzyme, the gold colloid sample aggregated with the very first addition of NaCl. The $\lambda_{max}$ of the enzyme-gold conjugates on the other hand, hardly changed, and the absence of additional peaks above 600 nm indicated that the conjugates remained well dispersed. The same profiles were obtained for all the conjugates tested as can be seen in FIG. 8 with no difference between the NfnB- and cys-NfnB-gold conjugates.

Enzyme Reactivity to Prodrugs Before and after Attachment to Colloidal Gold.

The retention of enzyme activity after immobilisation on the nanoparticles is essential, if the enzymes are to activate prodrug at the tumour site.

For these experiments, a 300 molar equivalents of enzyme were incubated with gold colloid, as this appeared to be the minimum amount of enzyme to cover the gold nanoparticle surface as determined by UV/Vis spectrometry, electrophoresis, and stability experiments. 3.206 nmol of the NfnB and cys-NfnB enzymes in ultra pure water were incubated with 1.5 ml 20 nm Naked Gold® (7.125×$10^{-3}$ μM) at a temperature of 4° C. overnight. As controls, the same treatment was carried out for NfnB and cys-NfnB in the absence of gold colloid. The next day the solutions were divided in half and each made up to a total volume of 970 μl using ultra pure water. To each sample, 20 μl of NADH (10 mM) were added and incubated at a temperature of 37° C. for 5 min. The absorbance spectra (750 nm-200 nm) were recorded every 1.5 min for 20 min upon the addition of 10 μl CB 1954 (10 mM) or 20 μl SN 23862 (5 mM) to the test sample, and an equivalent volume of dimethyl sulfoxide (DMSO) to the reference solution. The oxidation of NADH, measured as the decrease at 340 nm, was used as an indication of reactivity of the enzyme for the substrate. The reactivity experiments were done for enzyme: gold conjugate solutions and for enzymes free in solution.

The ability of both recombinant NfnB and cys-NfnB to activate the CB1954 prodrug, before and after attachment to the gold colloid were compared. The free enzyme is known to be active as a dimer in which each monomer is closely associated with a flavin mononucleotide (FMN) molecule, and has two substrate binding pockets as explained in Lovering et al. (Lovering A. L., Hyde E. I., Searle P. F. and White S. A., in *Journal of Molecular Biology*, 309: 203-213, 2001) or in Zenno et al. (Zenno S, Koike H, Tanokura M and Saigo' K, in *Journal of Biochemistry*, 120: 736-744, 1996). During the reaction of NfnB with substrate, NAD(P)H and nitroaromatic prodrug, 2 moles of NAD(P)H are oxidised and the prodrug is reduced to either the 2- or 4-hydroxylamine products.

The formation of hydroxylamine products was monitored at 420 nm using UV/Vis spectroscopy in the presence of enzyme and excess NADH as previously described. Oxidation of NADH by the nitroreductase in absence of prodrug was corrected for in this study by including both NADH and enzyme in the test and reference cells before addition of prodrug or solvent respectively.

It was observed that both the NADH and CB1954 substrates were consumed in the presence of recombinant NfnB, with the simultaneous production of the hydroxylamine product. The same experiment was performed for recombinant NfnB immobilised onto the gold colloid at a molar ratio of 87:1 enzymes to gold, to ensure that any activity measured was not due to excess enzyme free in solution. It was observed that the NfnB enzyme retained activity to the prodrug after immobilisation onto the gold. Bound cys-NfnB also retained activity to the prodrug. Surprisingly, both the immobilised NfnB and cys-NfnB enzymes retained more than 99% activity at a molar ratio of 87:1 enzymes: gold, when compared to the same concentration of enzyme free in solution as can be seen in Table 2.

TABLE 2

| Enzyme sample | Specific activity (µmol/min/mg) | Retained activity (%) |
|---|---|---|
| NfnB (unbound) | 0.169 | 100 |
| NfnB (bound to gold) | 0.168 | 99.5 |
| Cys-NfnB (unbound) | 0.211 | 100 |
| Cys-NfnB (bound to gold) | 0.209 | 99.3 |

The ability of the nitroreductases to retain nearly all of their activity after immobilisation onto the gold colloid indicated that the 3 dimensional structure was preserved without the requirement for additional stabilisers. Furthermore, activity results also suggested that the active sites of the enzymes were completely accessible to both solvent and substrate, which suggested that both the recombinant enzymes were orientated in such a way that the N-terminals were attached to the gold colloid exposing the enzyme active sites to the solvent, as previously depicted for cys-NfnB on a flat gold slide by Gwenin et al. (Gwenin, C. D., Kalaji, M., Williams, P. A. & Jones, R. M., in *Biosens and Bioelectron* 22, 2869-2875, 2007).

Coating 40 Nm Gold Colloid Particles with NfnB-Cys12.

The 40 nm gold colloid ($1.49 \times 10^{-4}$ nmol/ml, suspended in water, (BBInternational, UK) was incubated, at room temperature (18° C.) for 1 hour or at 4° C. for 17 hours, with varying ratios of enzyme concentration. The NfnB-cys12 protein solution (125 nmol/ml in PB buffer having a pH of 7.2) was purified and desalted as previously described Table 3 displays the molar ratio enzyme/gold and the concentrations of gold colloid and enzyme that were studied.

TABLE 3

| Ratio of Enzyme:Gold | Amount of enzyme solution added (nmol) | Amount of gold colloid added (ml) | Final concentration of gold colloid (nmol/ml) | Final concentration of enzyme (nmol/ml) |
|---|---|---|---|---|
| 100:1 | 0.0298 | 2 | 0.000148 | 0.0148 |
| 500:1 | 0.149 | 2 | 0.000148 | 0.0741 |
| 1000:1 | 0.298 | 2 | 0.000147 | 0.147 |
| 10 000:1 | 2.98 | 2 | 0.000147 | 1.47 |

Figure 9:
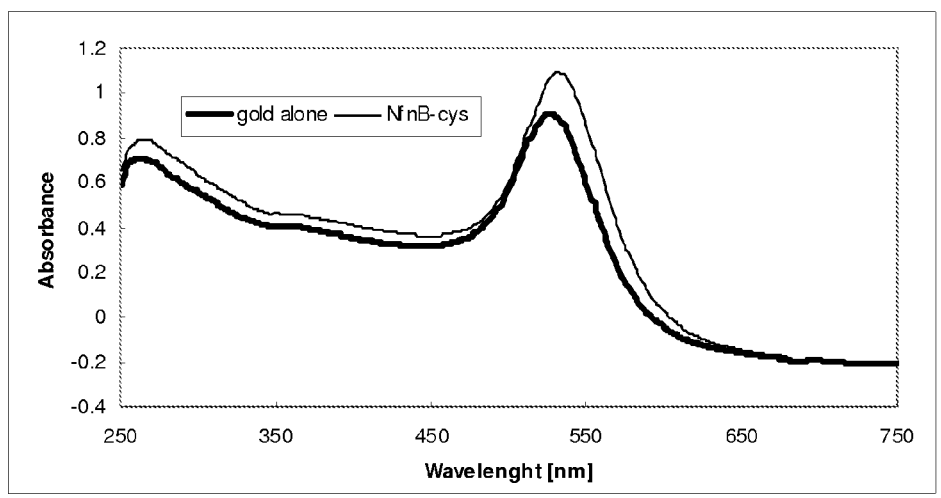
FIG. 9 represents the change in LSPR peak for 40 nm gold colloid alone and in the presence of NfnB-cys12 with a NfnB-cys12: gold ratio of 500:1 after 1 hour of incubation. Peak changes from 527 nm in absence of enzyme to 532 nm in presence of enzyme. The solid line represents gold alone and the dashed line represents gold and enzyme.

The 40 nm gold colloid was incubated for a period of time of one hour, with or without NfnB-cys12 and the UV-vis spectra were recorded in the region of 750 to 250 nm. Knowing that the 40 nm gold colloid absorbs at 527 nm in PB having a pH of 7.2, any changes in the Localised Surface Plasmon Resonance (LSPR) peak of the gold were noted and reported after incubation with NfnB-cys12. The results are reported in FIG. 9 where it is observed that for NfnB-cys12: gold ratio of 100:1 the 527 nm peak of gold alone is shifted to 532 nm in the presence of enzyme.

Figure 10:
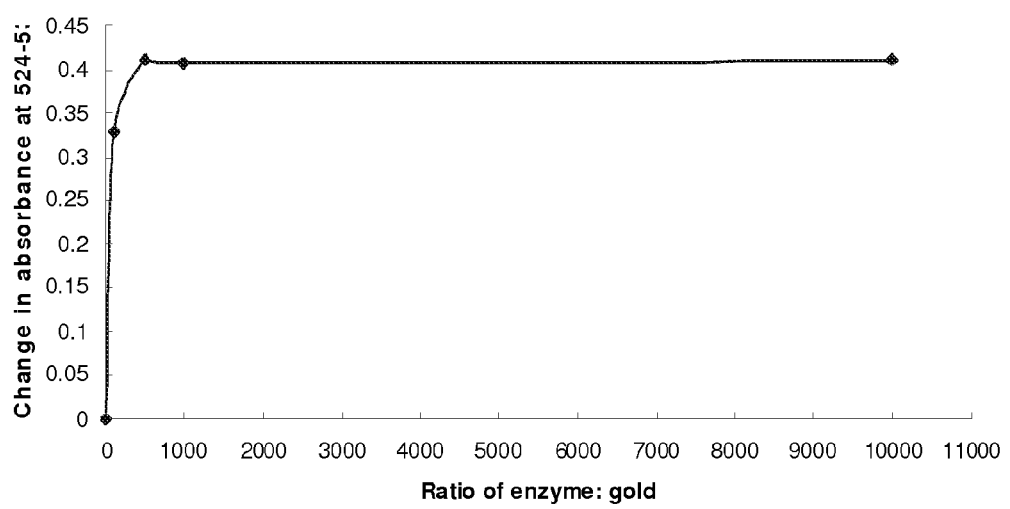
FIG. 10 represents change in gold colloid LSPR peak intensity as a function of NfnB-cys12: gold ratio in the 524-531 nm region for 40 nm gold particles.

Furthermore, the intensity of the LSPR peak increases with increasing concentrations of enzyme vs. gold colloid up to a 500:1 ratio of enzyme to gold as can be seen in FIG. 10. The LSPR peak intensity then reaches a maximum and remains stable for enzyme to gold ratio up to 10000:1 which is the largest ratio that was tested. These results suggest that the 40 nm gold colloid particles are completely coated at an enzyme to gold ratio of 500:1.

Figure 11:
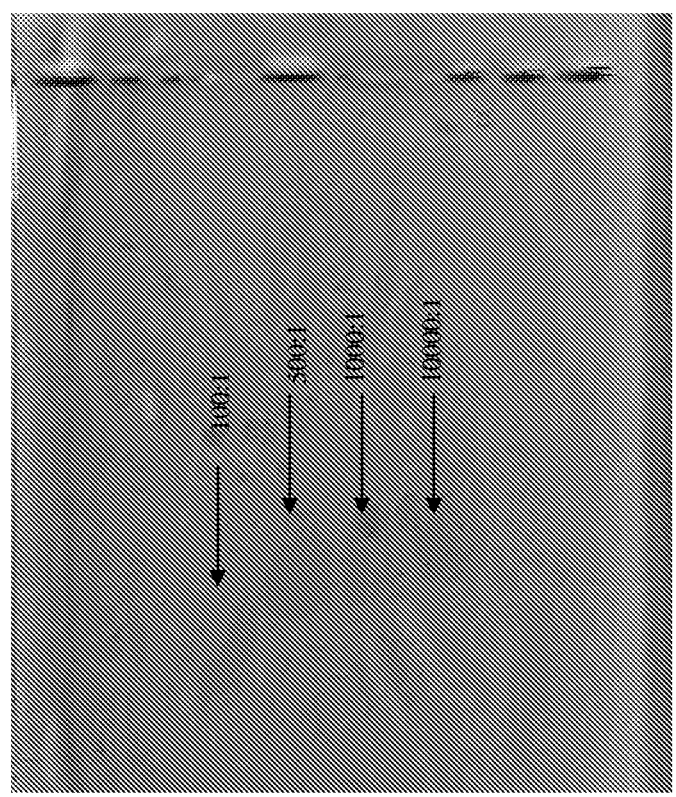
FIG. 11 represents a 0.7% agarose gel indicating the difference in migration of 40 nm gold colloid nanoparticles before and after incubation with different concentrations of NfnB-cys12 enzyme with ratios of enzyme: gold varying between 5:1 and 10000:1. Lane 1 is a blank, lane 2 represents gold alone, lane 3 an enzyme to gold ration of 100:1, lane 4 of 500:1, lane 5 of 100:1, lane 6 of 10000:1, lane 7 and lane 8 are blanks.

Agarose gel electrophoresis was also performed for the 40 nm particle of gold colloid alone and of gold colloid with various amounts of enzyme using the same method as that used for the 20 nm particles. The results are displayed in FIG. 11.

Synthesis of Au Coated Magnetic Particles: Au—Fe$_2$O$_3$ Synthesis.

0.1176 g Sodium Citrate were dissolved in 125 ml of H2O along with 0.0104 g Fe$_2$O$_3$ nanoparticles having a diameter of about 10 nm diameter, following the method of Massart (Massart R. IEEE Trans Magn 1981; 17(2):1247-8).

Figure 12:
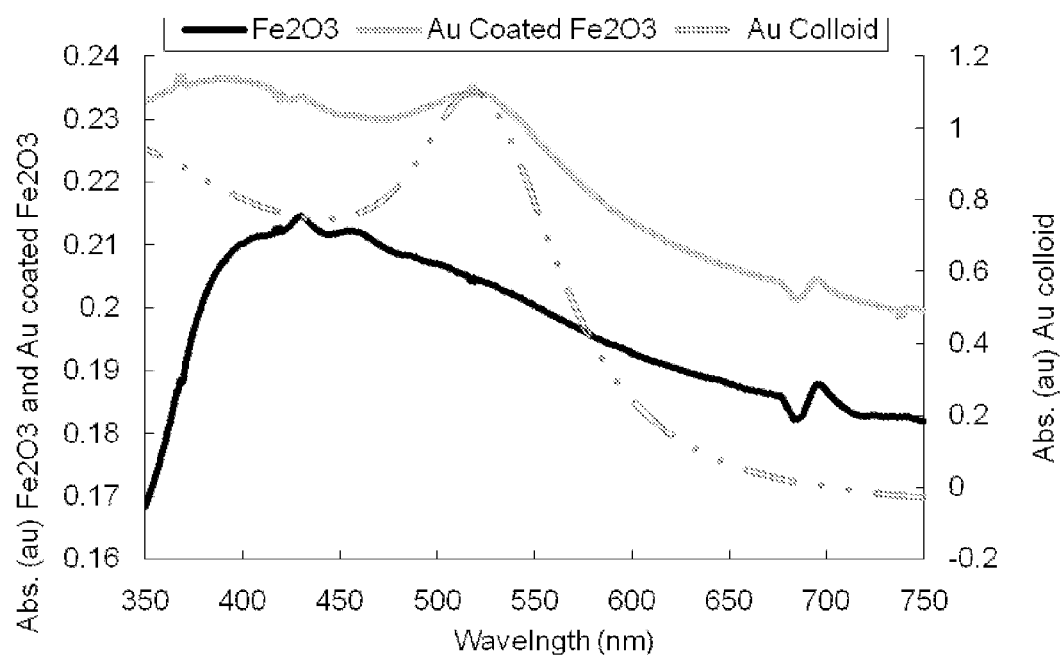
FIG. 12 represents UV spectra of the $Fe_2O_3$ coated and uncoated along with a reference pattern of colloidal gold.

The mixture was vigorously stirred for thirty minutes then heated to boiling. Upon boiling, $8.8290 \times 10^{-5}$ mol of HAuCl$_4$ dissolved in 5 ml of H$_2$O were immediately added. The solution was boiled for 15 minutes then the heat source was removed and the solution was kept under stirring until cool. Magnetic particles were isolated by magnetic decantation. They were washed several times with H$_2$O. FIG. 12 shows clearly that a gold coating has been successfully applied to the iron nanoparticles.

The invention claimed is:

1. A drug activator carrier comprising:
   a) particles having a metallic or metallic oxide core prepared from a paramagnetic material, said metallic core being coated with a coating material selected from polymer, metal or metal oxide;
   b) an enzyme, having reductase activity and modified to comprise a plurality of sulphur containing functional groups, bound onto the coating material coating the particles of a), and wherein said enzyme activates non-toxic pro-drugs into active and toxic drugs suitable for treating a disease;
   wherein said drug activator carrier allows targeted delivery of the toxic drug.

2. The drug activator carrier of claim 1 wherein the core is prepared from iron, nickel, cobalt or oxides thereof having a particle size of at most 100 nm.

3. The drug activator carrier of claim 1 wherein the coating material is a noble metal selected from the group consisting of gold, silver, platinum, palladium, iridium, rhenium, ruthenium, alloys and combinations thereof.

4. The drug activator carrier of claim 3 wherein the coating material coating the core is gold.

5. The drug activator carrier of claim 1, wherein the enzyme is modified by the addition of a plurality of cysteine amino acids.

6. The drug activator carrier of claim 1, wherein the enzyme is selected from bacterial NTRs.

7. The drug activator carrier of claim 1, wherein the coating material coating the core is gold, and the ratio of enzyme to gold ranges between 100:1 and 500:1.

8. The drug activator carrier of claim 7, wherein the ratio is between 200:1 and 400:1.

9. The drug activator carrier of claim 1, having a final size of at most 100 nm.

10. The drug activator carrier of claim 1, wherein the core is prepared from iron having a particle size of at most 100 nm.

11. The drug activator carrier of claim 1, wherein the enzyme is a nitroreductase.

12. The drug activator carrier of claim 1, having a final size of at most 60 nm.

13. A method for delivering an active drug to a desired position comprising applying a magnetic field gradient to direct a drug activating carrier according to claim 1 to the desired location.

14. A method according to claim 13 for the treatment of diseases.

15. A method according to claim 13 for the treatment of cancer.

16. A method for preparing a drug activating carrier that comprises the steps of:
   a) providing nanoparticles of a paramagnetic material;
   b) coating said particles with a metal or metal oxide or polymer;
   c) immobilising an enzyme capable of transforming a non toxic prodrug into an active and toxic drug for treating a disease, by chemical bonding between the enzyme and the coating wherein the enzyme has reductase activity and modified to comprise a plurality of sulphur containing functional groups.

* * * * *